(12) United States Patent
Mitschke et al.

(10) Patent No.: US 7,010,095 B2
(45) Date of Patent: Mar. 7, 2006

(54) APPARATUS FOR DETERMINING A COORDINATE TRANSFORMATION

(75) Inventors: Matthias Mitschke, Nuremberg (DE); Dieter Ritter, Fuerth (DE); Anders Steiner, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 42 days.

(21) Appl. No.: 10/347,821

(22) Filed: Jan. 21, 2003

(65) Prior Publication Data

US 2003/0179856 A1 Sep. 25, 2003

(30) Foreign Application Priority Data

Jan. 21, 2002 (DE) ................................ 102 02 091

(51) Int. Cl.
*G01D 18/00* (2006.01)
(52) U.S. Cl. .................... 378/162; 378/204; 378/205; 378/207; 600/426; 600/429
(58) Field of Classification Search ................ 378/162, 378/163, 164, 204, 205, 207; 600/425, 426, 600/429

See application file for complete search history.

(56) References Cited

U.S. PATENT DOCUMENTS

| | | | |
|---|---|---|---|
| 5,873,822 A * | 2/1999 | Ferre et al. .................. 600/407 |
| 5,944,663 A | 8/1999 | Kuth et al. ................... 600/411 |
| 6,163,589 A * | 12/2000 | Vartanian ......................... 378/7 |
| 6,285,902 B1 * | 9/2001 | Kienzle et al. .............. 600/427 |
| 6,428,547 B1 * | 8/2002 | Vilsmeier et al. ............ 606/130 |
| 6,470,207 B1 * | 10/2002 | Simon et al. ................ 600/426 |
| 6,493,574 B1 * | 12/2002 | Ehnholm et al. ............ 600/429 |
| 6,527,443 B1 * | 3/2003 | Vilsmeier et al. ............ 378/205 |
| 6,585,412 B1 * | 7/2003 | Mitschke ..................... 378/207 |
| 6,694,168 B1 * | 2/2004 | Traxel et al. ................ 600/426 |

FOREIGN PATENT DOCUMENTS

| | | |
|---|---|---|
| DE | 199 09 816 | 5/2000 |
| DE | 199 17 867 | 11/2000 |
| DE | 199 51 502 | 1/2001 |

* cited by examiner

*Primary Examiner*—Allen C. Ho
(74) *Attorney, Agent, or Firm*—Schiff Hardin LLP

(57) ABSTRACT

An apparatus for determining a coordinate transformation for mixing an image of a first subject into an X-ray image of a second subject has an arrangement for fastening the apparatus to the second subject, markers that can be acquired by a navigation system, and X-ray-positive marks. The positions and orientations of the markers that can be acquired with the navigation system and the positions and orientations of the X-ray-positive marks relative to one another are thus known, so a coordinate transformation can be determined between a coordinate system allocated to the navigation system and a coordinate system allocated to the X-ray image. Thus an image of the first subject that can be acquired with the navigation system can be mixed into an X-ray image of the second subject.

3 Claims, 1 Drawing Sheet

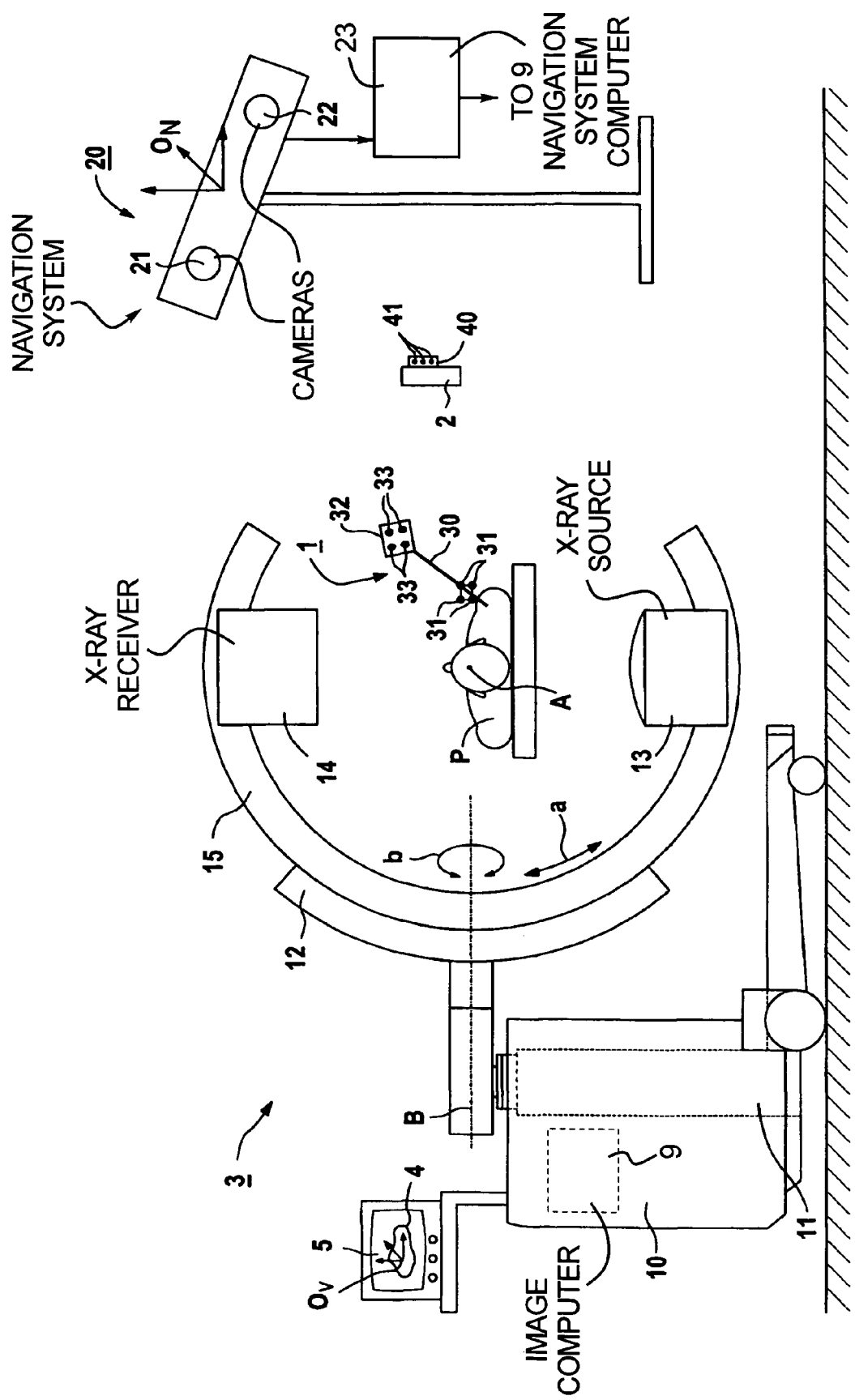

APPARATUS FOR DETERMINING A COORDINATE TRANSFORMATION

BACKGROUND OF THE INVENTION

1. Field of the Invention

The present invention is directed to an apparatus for determining a coordinate transformation for mixing an image of a first subject into an X-ray image of a second subject.

2. Description of the Prior Art

Navigation is being increasingly practiced for supporting medical interventions at living subjects, this being defined as the guidance of a medical instrument relative to a living subject or relative to a tissue region of the living subject being treated, that is supported with optical image information. An image of the instrument is thereby mixed into an image of the living subject acquired with an X-ray apparatus, such as a 2D or 3D image. In this way, an operator can guide an instrument that has at least partly penetrated into the living subject, the tip of which is no longer directly visible because it has penetrated into body tissue. This guidance ensues relative to the tissue region of the living subject to be treated on the basis of the image information without a risk of unintentional harm to the life form.

In order to enable such a navigation-guided intervention, i.e. in order to be able to mix an image of the instrument into image information of a living subject with exact position and attitude, it is necessary to produce a mathematical relationship in the form of a coordinate transformation between the coordinate system of the image information of the living subject, or a coordinate system of the reconstructed volume of the subject and a coordinate system with respect to which the positions of the instrument to be navigated are defined. Heretofore, artificial marks or anatomical marks, for example pronounced bone structures, have sometimes been defined at the subject. The anatomical or artificial marks must be clearly visible in the image information of the subject registered with the X-ray apparatus and must be easily accessible at the subject. The artificial marks, for example, are secured to the skin surface of the life form in order to be able to undertake a procedure referred to as a registration, which is understood as the determination of the spatial transformation rule between the coordinate system in which the positions of the instrument to be navigated are indicated and the image information or of the subject the reconstructed volume thereof, employed for the navigation. The marks usually must be individually approached with the instrument in order to be able to determine the coordinate transformation between the two coordinate systems. The registration of the marks is therefore a relatively time-consuming process for an operator.

German OS 199 09 816, for example, discloses a navigation system for the implementation and support of surgical interventions, wherein the system has access to an image data bank for pre-operatively prepared nuclear magnetic resonance and/or computer tomography data. Marks that are visible in the images of the patient are arranged at the patient. Ultimately, a transformation relationship between the images made of the patient and the coordinate system allocated to the navigation system can be produced in a registration procedure wherein the marks arranged at the patient are approached with an instrument, the positions of which can be determined with a navigation system.

German OS 199 17 867 discloses an apparatus for determining a coordinate transformation that includes means (which are not specified in detail) for fastening the apparatus to a subject, which can be a patient. The apparatus has an adapter with markers that can be acquired by a navigation system and also has a reference structure with X-ray-positive marks. A coordinate transformation between a coordinate system allocated to a navigation system and a coordinate system allocated to an X-ray image can be produced on the basis of the reference structure and the adapter.

German OS 195 15 748 discloses a therapy apparatus for treating a body region of a patient with acoustic waves, wherein the spatial allocation of the patient and a source of acoustic waves of the therapy apparatus (required for the treatment) relative to one another is accomplished by means of a workstation and with the use of 3D navigation systems on the basis of images of the body region of the patient to be treated that are acquired with an imaging device independently of the therapy apparatus, and that are displayed on a picture screen of the workstation.

German OS 199 51 502 also discloses a system that has an image pick-up device for acquiring images of a patient and a navigation system for determining the position of the image pick-up device as well as for determining the position of a subject to be moved relative to the patient. By determining the position of the instrument relative to the image pick-up device, an image of the medical instrument can be mixed into an image of the patient acquired with the image pick-up device.

SUMMARY OF THE INVENTION

An object of the present invention is to provide an apparatus of the type initially described wherein the determination of the coordinate transformation is simplified.

This object is inventively achieved in an apparatus for determining a coordinate transformation for mixing an image of a first subject into an X-ray image of a second subject that has an arrangement for fastening the apparatus to the second subject, markers that can be acquired by a navigation system and that are connected to the arrangement for fastening, and X-ray-positive marks connected to the arrangement for fastening. The orientations and positions of the markers that can be acquired with the navigation system and the X-ray-positive marks relative to one another are known. The X-ray positive marks can be remote from the arrangement for fastening. According to the invention, the apparatus also is secured to the second subject, for example to a living subject or tissue of the subject to be examined, with the arrangement for fastening. The coordinates of the markers of the apparatus, that are detectable with a navigation system in a coordinate system allocated to the navigation system, can be subsequently determined with the navigation system. As a result of the positions and orientations of the markers that are detectable with the navigation system and the X-ray-positive marks of the apparatus relative to one another being known, the coordinates of the X-ray-positive marks also can be determined in the coordinate system allocated to the navigation system.

When an X-ray image of the subject provided with the apparatus, or of the tissue of the subject to be treated that is provided with the apparatus, is finally acquired, then the X-ray-positive marks of the apparatus that are usually imaged therein can be detected either manually or, preferably, fully automatically, and their coordinates in a coordinate system allocated to the X-ray image can be determined. Subsequently, a coordinate transformation between the coordinate system allocated to the X-ray image and the coordinate system allocated to the navigation system—and wherein the coordinates of the X-ray-positive marks of the apparatus are known—can be determined in a simple way. For navigation of a first subject, for example an instrument, relative to the tissue of the subject to be treated on the basis of the X-ray image of the tissue, accordingly, the instrument employed therefor need only be provided with markers that are detectable with the navigation system, so that its coordinates in the coordinate system allocated to the navigation system always can be determined. Due to the known coordinate transformation between the coordinate system allocated to the navigation system and the coordinate system allocated to the X-ray image, finally, an image of the instrument can be mixed into the X-ray image of the tissue for supporting the medical intervention. It is especially advantageous that the X-ray-positive marks can be removed from the apparatus, which usually occurs after the determination of the coordinate transformation. In this way, the X-ray-positive marks do not impede a physician during the medical intervention at the tissue of the subject to be treated. As long as the apparatus with the markers that are detectable with the navigation system continues to remain in the tissue, movements of the tissue to be treated—whether due to repositioning or due to periodic motions, for example as a result of respiration—also can be acquired with the navigation system and correspondingly taken into consideration in the mixing of the image of the instrument into the X-ray image.

In a version of the invention the arrangement for fastening as well as the markers of the apparatus that are detectable with the navigation system are X-ray-transparent. An imaging of these items in an X-ray image of the subject is avoided in this way, so that no disturbing superimpositions occur.

DESCRIPTION OF THE DRAWINGS

The FIGURE is a schematic illustration of an exemplary embodiment of the invention.

DESCRIPTION OF THE PREFERRED EMBODIMENTS

The FIGURE illustrates the employment of the inventive apparatus 1 for determining a coordinate transformation for mixing an image of a medical instrument 2 into an X-ray image 4 of a body part of a patient P that is generated with an X-ray device 3.

The X-ray device 3 is a known C-arm X-ray device 3 with a device cart 10 having a lifting mechanism 11 to which a support 12 is connected. A C-arm 15 that is provided with an X-ray source 13 and an X-ray receiver 14 and that is adjustable (see double arrow 'a') around the orbital axis A along its circumference—isocentrically in the present exemplary embodiment—is seated at the support 12. Together with the support 12, the C-arm 15 can be isocentrically swiveled around its angulation axis B in the directions of the double arrow 'b'.

2D projections of body regions of the patient P or a volume dataset of a body region of the patient P can be acquired with the C-arm X-ray device 3 in a known way. For acquiring a volume dataset of a body region of the patient P, the C-arm 15 is moved either around its orbital axis A or around its angulation axis B in an angular range of approximately 190°, with approximately 50 to 100 2D projections of the respective body region being acquired from different projection directions, the volume dataset being reconstructed from these projections in a known way. In a way that is also known, 2D or 3D X-ray images of the acquired body region of the patient P can be generated from the volume dataset and displayed on a viewing device 5.

The FIGURE also shows a navigation system 20 that has two cameras 21, 22. For supporting a navigation-guided intervention at the patient P, the inventive apparatus 1 is secured to the patient P, as shown in the FIGURE. The apparatus 1 has a rod 30 formed of an X-ray-transparent material that is secured to the humerus of the patient P in a way not shown in detail. To this end, the brachium of the patient P has been provided with a hole into which the one end of the rod 30 has been introduced. Four X-ray-positive marks 31 are also arranged at the rod 30 so as to be situated (in this example) close to the humerus of the patient P, representing the operative field. The apparatus 1 also has an X-ray-transparent marker plate 31 at an end remote from the patient P that is provided with X-ray-transparent markers 33 that can be detected by the navigation system 20. The markers 33 as well as the X-ray-positive marks 31 of the apparatus 1 are arranged relative to one another in a defined way so that the coordinates of the X-ray-positive marks 31 of the apparatus 1 can be identified and are thus known in a Cartesian coordinate system $O_N$ allocated to the navigation system 20 due to the acquisition of the coordinates of the markers 33 of the apparatus 1 with the cameras 21, 22 of the navigation system 20. The coordinates of the markers 33 as well as the coordinates of the X-ray-positive marks 31 are identified by a computer 23 allocated to the navigation system 20, this identification being with respect to the coordinate system $O_N$ on the basis of the camera images acquired from the markers 33.

When a volume dataset of the region around the humerus of the patient P is acquired with the assistance of the C-arm X-ray device 3 in the course of the navigation-guided intervention, then the X-ray-positive marks 31 are likewise contained in the volume dataset as images, by virtue of communication between the computer 33 and an image computer 9 allocated to the C-arm X-ray device 3, and can be imaged as warranted in a 2D or 3D X-ray image 4 generated from the volume dataset by the computer 9. The coordinates of the marks 31 contained in the volume dataset as images are determined either manually or fully automatically in a coordinate system $O_V$ allocated to the volume dataset, so that a coordinate transformation between the coordinate system $O_N$ allocated to the navigation system—and wherein the coordinates of the X-ray-positive marks 31 are known—and the coordinate system $O_V$ allocated to the reconstructed volume—and wherein the X-ray-positive marks 31 are contained as images—is determined on the basis of the coordinates of the X-ray-positive marks 31 contained in the volume dataset as images. Since an X-ray image employed for the navigation is generated from the volume dataset, the coordinate system $O_V$ is also allocated to the X-ray image employed, so that images of subjects whose coordinates in the coordinate system $O_N$ allocated to the navigation system can be mixed into the X-ray image upon employment of the identified coordinate transformation.

In order to be able to navigate an instrument 2 needed for the treatment of the patient P on the basis of X-ray images displayed at the viewing device 5, a marker plate 40 having markers detectable by the navigation system 20 is arranged at the instrument 2 in a defined way. As a result, the coordinates of the instrument 2 in the coordinate system $O_N$ allocated to the navigation system always can be determined during the navigation-guided intervention, so that, by means of the identified coordinate transformation between the coordinate system $O_N$ allocated to the navigation system and the coordinate system $O_V$ allocated to the volume dataset, an image of the instrument can be mixed into an X-ray image 4 of the region of the brachium of the patient P that is generated from the volume dataset and displayed on the viewing device 5.

The determination of the volume dataset of the patient P employed for the navigation as well as the determination of the coordinates of the markers 33 detectable with the navigation system 20, of the X-ray-positive marks 31 as well as the determination of the coordinate transformation between the coordinate systems $O_N$ of the navigation system and $O_V$ of the volume dataset preferably ensue intra-operatively, i.e. during the surgical intervention at the patient P.

The X-ray-positive marks 31, moreover, can be remote from the apparatus 1, so that they do not disturb a surgeon (not shown in the FIGURE) during the treatment of the patient P. Because the apparatus 1 with the markers 33 detectable by the navigation system 20 can remain at the patient, movements on the part of the patient P, particularly movements of the region of the operative field, can be acquired with the navigation system and be correspondingly taken into consideration in the mixing of an image of the instrument 2 into an X-ray image 4 generated from the volume dataset.

The invention has been explained above with reference to the example of an optical navigation system 20. However, the navigation system need not necessarily be an optical navigation system. An electromagnetic navigation system or a navigation system based on acoustic waves alternatively can be employed. In such cases, the optical markers 33 or 41 are replaced by, for example, electromagnetic transmitters or acoustic transmitters, and the cameras 21, 22 are to be replaced by suitable receivers for electromagnetic waves or receivers for acoustic waves.

The X-ray device, moreover, need not necessarily be a C-arm X-ray device.

Further, the X-ray-positive marks 31 need not necessarily be remote from the apparatus 1.

The arrangement 30 for fastening the apparatus and the markers 33 that are detectable with the navigation system 20 need not necessarily be X-ray-transparent.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for determining a coordinate transformation for mixing an image of a first subject into an X-ray image of a second subject for use with a navigation system and an X-ray imaging system, comprising:
    markers which are acquirable by a navigation system;
    an arrangement adapted to physically secure said markers to said second subject; and
    X-ray positive marks acquirable by said X-ray imaging system connected to said arrangement with respective positions and orientations of said markers and said X-ray positive marks relative to each other being known, and said X-ray positive marks being removable from said arrangement.

2. An apparatus as claimed in claim 1 wherein said arrangement is composed of X-ray transparent material.

3. An apparatus as claimed in claim 1 wherein said markers are X-ray transparent.

* * * * *